US010422766B2

(12) United States Patent
Cheng

(10) Patent No.: US 10,422,766 B2
(45) Date of Patent: Sep. 24, 2019

(54) MANUFACTURING DEVICE AND MANUFACTURING METHOD OF TEST STRIP

(71) Applicant: NATIONAL TSING HUA UNIVERSITY, Hsinchu (TW)

(72) Inventor: Chao-Min Cheng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 216 days.

(21) Appl. No.: 15/649,944

(22) Filed: Jul. 14, 2017

(65) Prior Publication Data
US 2018/0275087 A1    Sep. 27, 2018

(30) Foreign Application Priority Data
Mar. 24, 2017  (TW) .............................. 106109941 A

(51) Int. Cl.
| G01N 27/327 | (2006.01) |
| G01N 33/52 | (2006.01) |
| G01N 33/68 | (2006.01) |
| B01L 3/00 | (2006.01) |
| G01N 27/00 | (2006.01) |
| G01N 33/00 | (2006.01) |

(52) U.S. Cl.
CPC ........ *G01N 27/3272* (2013.01); *B01L 3/5023* (2013.01); *B01L 3/523* (2013.01); *B01L 3/527* (2013.01); *G01N 33/521* (2013.01); *G01N 33/68* (2013.01); *B01L 2200/027* (2013.01); *B01L 2300/047* (2013.01); *B01L 2300/0825* (2013.01); *B01L 2400/0487* (2013.01); *G01N 27/00* (2013.01); *G01N 33/00* (2013.01)

(58) Field of Classification Search
CPC ................................. G01N 32/72; C12M 1/36
See application file for complete search history.

(56) References Cited

U.S. PATENT DOCUMENTS

2004/0219661 A1*  11/2004  Chen ................. B01L 3/502715
                                                    435/286.5
2008/0035485 A1    2/2008  Chen

FOREIGN PATENT DOCUMENTS

| TW | 200424522 A | 11/2004 |
| TW | I316873 B | 11/2009 |

\* cited by examiner

*Primary Examiner* — Dah-Wei D. Yuan
*Assistant Examiner* — Andrew J Bowman
(74) *Attorney, Agent, or Firm* — Muncy, Geissler, Olds & Lowe, P.C.

(57) ABSTRACT

A manufacturing device and a manufacturing method of a test strip. The manufacturing device includes a fluid push module, a fluid flow module and a fluid output module. The fluid push module includes an actuator and a transmission unit. The transmission unit has at least a fluid delivery member. The fluid flow module includes a reagent storage unit and a reagent delivery unit. The reagent storage unit has at least one reagent storage chamber. The reagent delivery unit has at least one drain chamber, at least one first infusion line, at least a second infusion line and a plurality of check valves. The fluid output module includes a plurality of reagent outlets and a reagent output unit, and one end of each of the reagent outlets is configured with an inner recess. The reagent output unit has a plurality of channels corresponding to the reagent outlets.

15 Claims, 9 Drawing Sheets

MANUFACTURING DEVICE AND MANUFACTURING METHOD OF TEST STRIP

CROSS REFERENCE TO RELATED APPLICATIONS

This Non-provisional application claims priority under 35 U.S.C. § 119(a) on Patent Application No(s). 106109941 filed in Taiwan, Republic of China on Mar. 24, 2017, the entire contents of which are hereby incorporated by reference.

BACKGROUND

Technology Field

The present disclosure relates to a manufacturing device and a manufacturing method of a test strip.

Description of Related Art

In the recent years, the food safety, such as the remained toxic materials, pesticides, unhealthy additives, process pollutants and the likes, is always a concerned issue, so that the food safety detections have become more and more important. Therefore, it is desired to effectively detect out the improper additives before eating the food products. Besides, since the stress of modern life and the irregular living habits, the patients with high blood sugar, high blood pressure and high blood lipids, and their derived diseases are increasing. Therefore, the immediate detection of physiological condition is important. This immediate detection can help the users to confirm their own health statuses, and the patients can improve the therapeutic effect and realize the curing progress through the physiological status detection.

In view of this, the home fast screen test strip has been disclosed and become popular. Currently, various test strips have appeared in the market, and the manufacturing devices of these test strips are also introduced. However, in the conventional manufacturing device of test strips, the cost for manufacturing the test strips is higher and the manufacturing speed thereof is slow. In addition, the conventional test strips are mostly produced in a mass production model, which is to produce a single type of test strips so as to reduce the cost. In fact, these test strips made by mass production model are not attractive to some consumers with a specific need. Most of the existing test strips are still sugar test strips and pregnant test strips, which have many potential customers in market. More importantly, since the equipment for manufacturing the test strips is very large and expensive, the manufacturer can only produce the test strips of a single type in the factory. Only the medical or detection institutes will use these test strips, and these test strips are not attractive to the common customers.

Therefore, it is desired to provide a manufacturing device of a test strip that has a smaller size by utilizing simple micro control mechanism, a reduced manufacturing cost by lowering the reagent dot, a high manufacturing capacity, and a wider application field.

SUMMARY

In view of the foregoing, the present disclosure provides a manufacturing device of a test strip, which includes a fluid push module, a fluid flow module and a fluid output module. The fluid push module includes an actuator and a transmission unit. The actuator is connected to the transmission unit, and the transmission unit has at least a fluid delivery member. The fluid delivery member is disposed at one end of the transmission unit. The fluid flow module includes a reagent storage unit and a reagent delivery unit. The reagent storage unit has at least a reagent storage chamber, and the reagent delivery unit has at least a drain chamber, at least a first infusion line, at least a second infusion line and a plurality of check valves. The fluid delivery member is disposed in the drain chamber, and the first infusion line is disposed between the reagent storage chamber and the drain chamber and communicates the reagent storage chamber and the drain chamber. The check valves are disposed at one ends of the first infusion line and the second infusion line. The fluid output module includes a plurality of reagent outlets and a reagent output unit. One end of each reagent outlet is configured with an inner recess, and a reagent flow direction is opposite to a gravity direction. The reagent output unit has a plurality of channels corresponding to the reagent outlets, and each of the channels is connected to another end of each of the reagent outlets opposite to the inner recess. The second infusion line is disposed between the drain chamber and the reagent output unit and communicates the drain chamber and the reagent output unit.

In one embodiment, the reagent outlets are replaceable.

In one embodiment, the check valves includes a first check valve and a second check valve. The first check valve is disposed at one end of the first infusion line, and the second check valve is disposed at one end of the second infusion line.

In one embodiment, the fluid flow module and the fluid output module together form at least a reagent transmission path, and the reagent transmission path is isolated.

In one embodiment, multiple of the reagent outlets arranged in a row have a common one of the channels.

In one embodiment, the manufacturing device further includes at least a first sensing module disposed at one end of a back-and-forth path of the transmission unit.

In one embodiment, the manufacturing device further includes at least a second sensing module disposed at another end of the back-and-forth path of the transmission unit, which is opposite to the first sensing module.

In one embodiment, the manufacturing device further includes a control module for controlling the actuator.

In one embodiment, the manufacturing device further includes a pressure module disposed corresponding to the reagent outlets.

In one embodiment, the fluid flow module further includes a reagent supply unit having at least a supply tank, and the supply tank is communicated with the reagent storage chamber.

The present disclosure also provides a manufacturing method of a test strip applied to the above-mentioned manufacturing device of a test strip. The manufacturing method includes the following steps of: the actuator driving the transmission unit and the fluid delivery member; the fluid delivery member moving away from the second infusion line so that the drain chamber drains a reagent from the reagent storage chamber and the reagent flows from the first infusion line to the drain chamber; the fluid delivery member moving toward the second infusion line so that the reagent in the drain chamber flows to the reagent outlets through the second infusion line and the reagent output unit in order; and the reagent contacting with a plurality of hydrophilic areas of a substrate, wherein the reagent penetrating into the substrate by capillary phenomenon and overcoming gravity so as to form the test strip.

In one embodiment, the check valves includes a first check valve and a second check valve. The first check valve is disposed at one end of the first infusion line, and the second check valve is disposed at one end of the second infusion line. When the fluid delivery member moves away from the second infusion line, the second check valve stops the reagent flowing from the reagent output unit to the drain chamber. When the fluid delivery member moves toward the second infusion line, the first check valve stops the reagent flowing from the drain chamber to the reagent storage chamber.

In one embodiment, the fluid flow module and the fluid output module together form at least a reagent transmission path, and the reagent transmission path is isolated. When the fluid delivery member moves away from the second infusion line, the reagent stored in the reagent storage chamber flows from the reagent storage chamber to the drain chamber through the first infusion line. When the fluid delivery member moves toward the second infusion line, the reagent stored in the drain chamber flows from the drain chamber to the reagent outlets through the second infusion line and the reagent output unit in order.

In one embodiment, the manufacturing device further includes a control module for controlling the actuator to operate, to stop or to reverse operate.

In one embodiment, the manufacturing device further includes at least a first sensing module disposed at one end of a back-and-forth path of the transmission unit. When the first sensing module senses a sense target of the transmission unit, the first sensing module outputs a first sensing signal to the control module, and the control module controls the actuator to stop.

In one embodiment, the manufacturing device further includes at least a second sensing module disposed at another end of the back-and-forth path of the transmission unit, which is opposite to the first sensing module. When the second sensing module senses the sense target of the transmission unit, the second sensing module outputs a second sensing signal to the control module, and the control module controls the actuator to stop.

As mentioned above, the manufacturing device of a test strip can adjust the stepwise delivery amount by controlling the actuator and the transmission unit in the back-and-forth path, thereby achieving the precisely control and micro amount output of the reagent. In addition, the direction of the inner recess and the output direction of the reagent are opposite to the gravity direction, so that the output amount of the reagent can be more precisely controlled. This design can prevent the excess output of the reagent, which may overflow from the hydrophilic area of the substrate.

BRIEF DESCRIPTION OF THE DRAWINGS

The disclosure will become more fully understood from the detailed description and accompanying drawings, which are given for illustration only, and thus are not limitative of the present disclosure, and wherein.

DETAILED DESCRIPTION OF THE DISCLOSURE

The present disclosure will be apparent from the following detailed description, which proceeds with reference to the accompanying drawings, wherein the same references relate to the same elements.

Figure 1A:
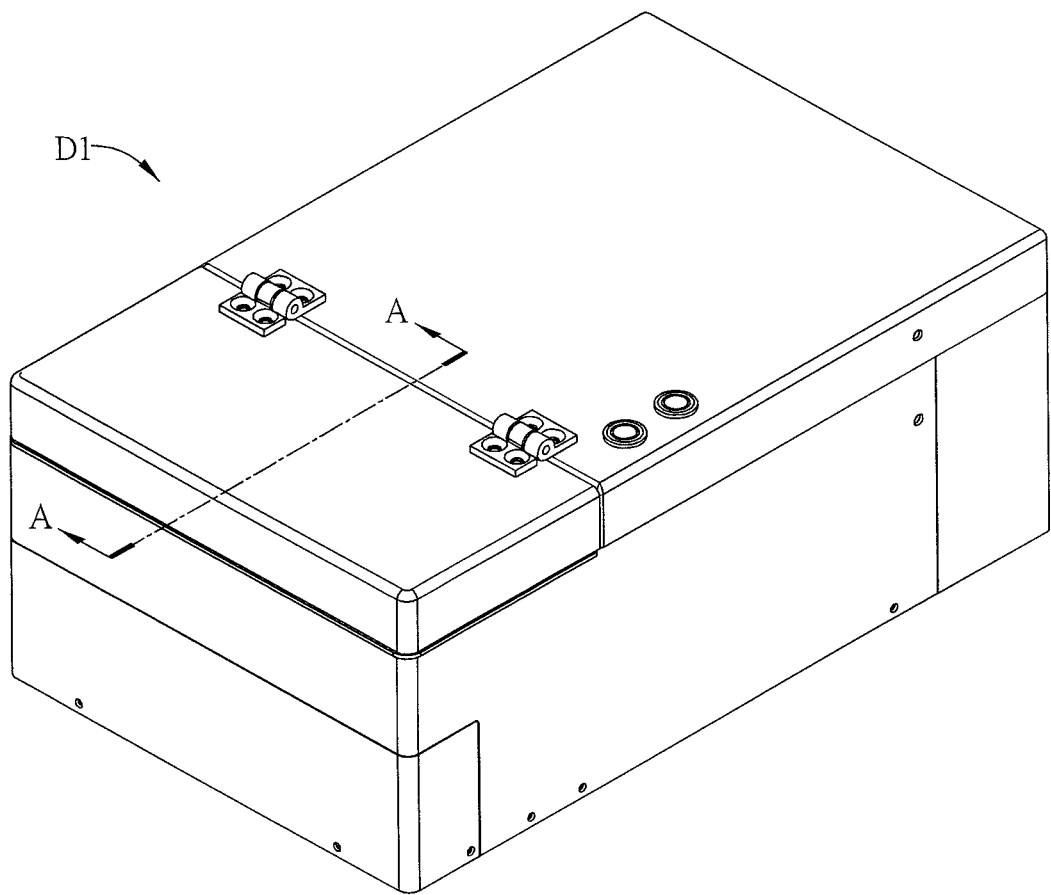
FIGS. 1A and 1B are schematic diagrams showing a manufacturing device of a test strip according to an embodiment of the disclosure.
Figure 1B:
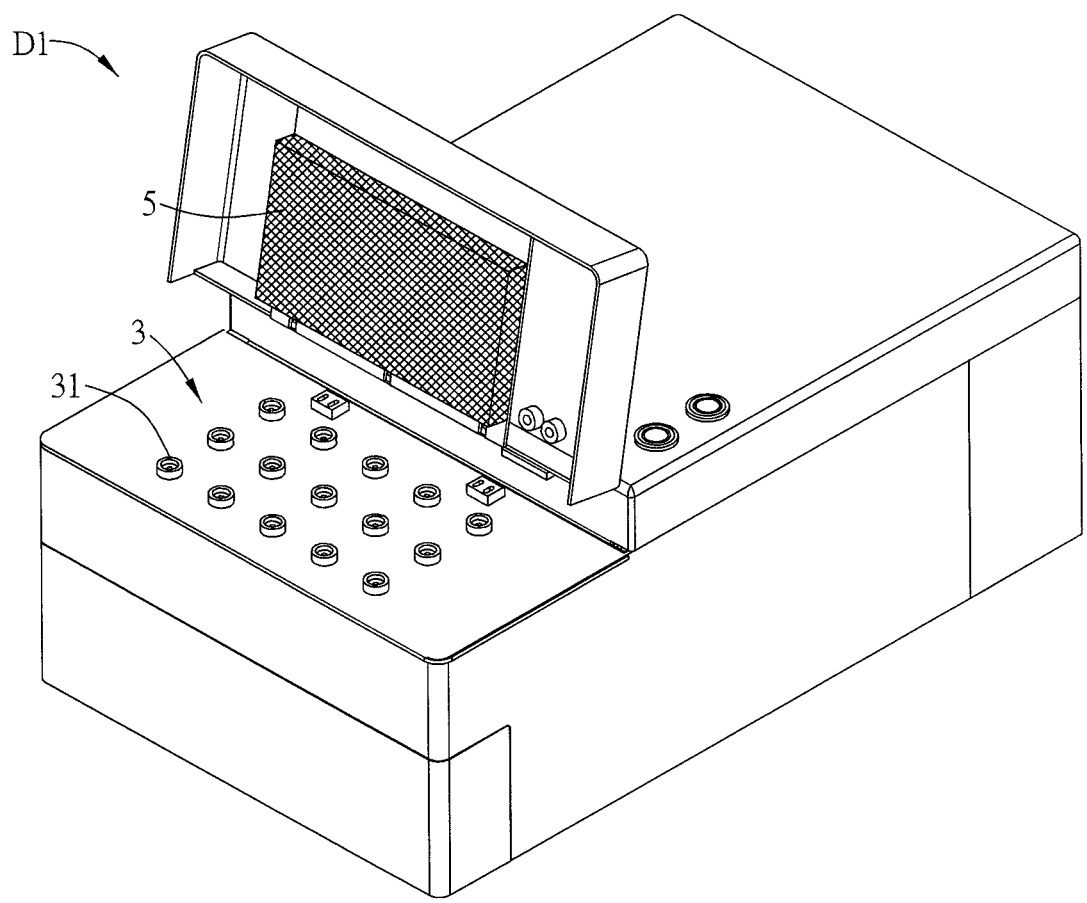
Figure 2:
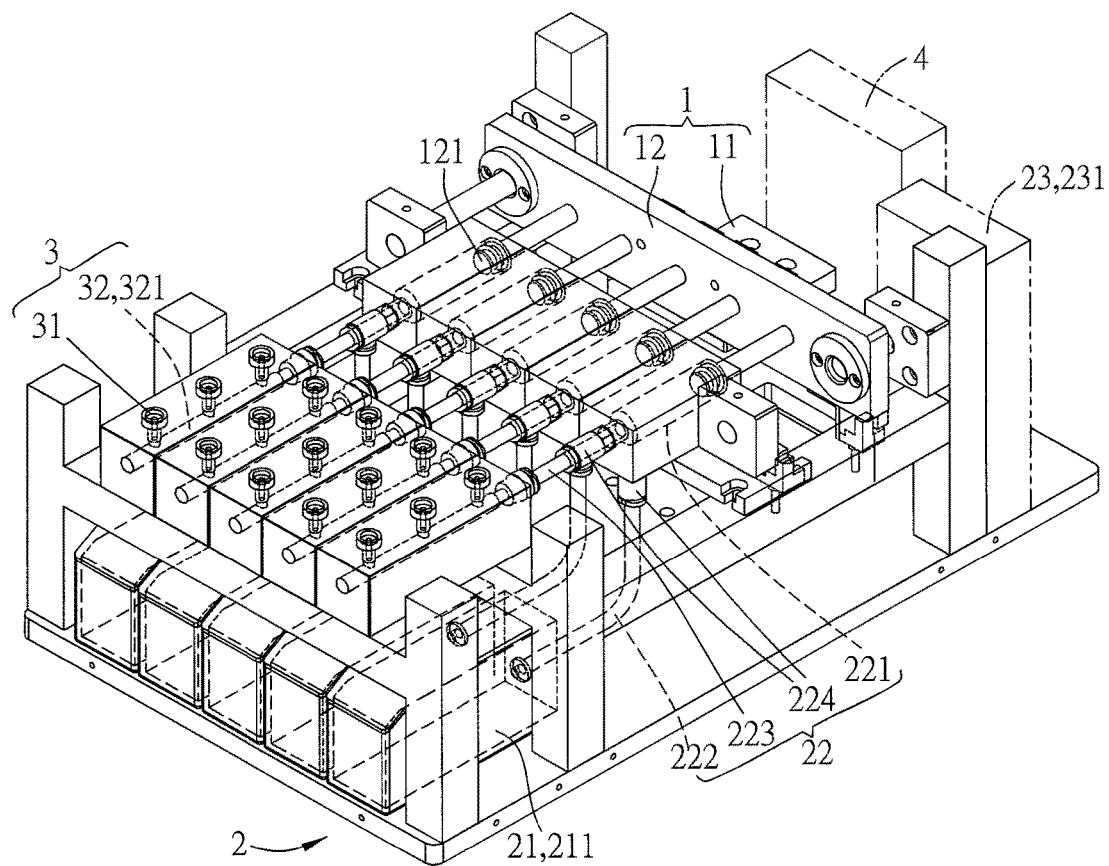
FIG. 2 is a schematic diagram showing the internal mechanisms of the manufacturing device of FIG. 1A.
Figure 3A:
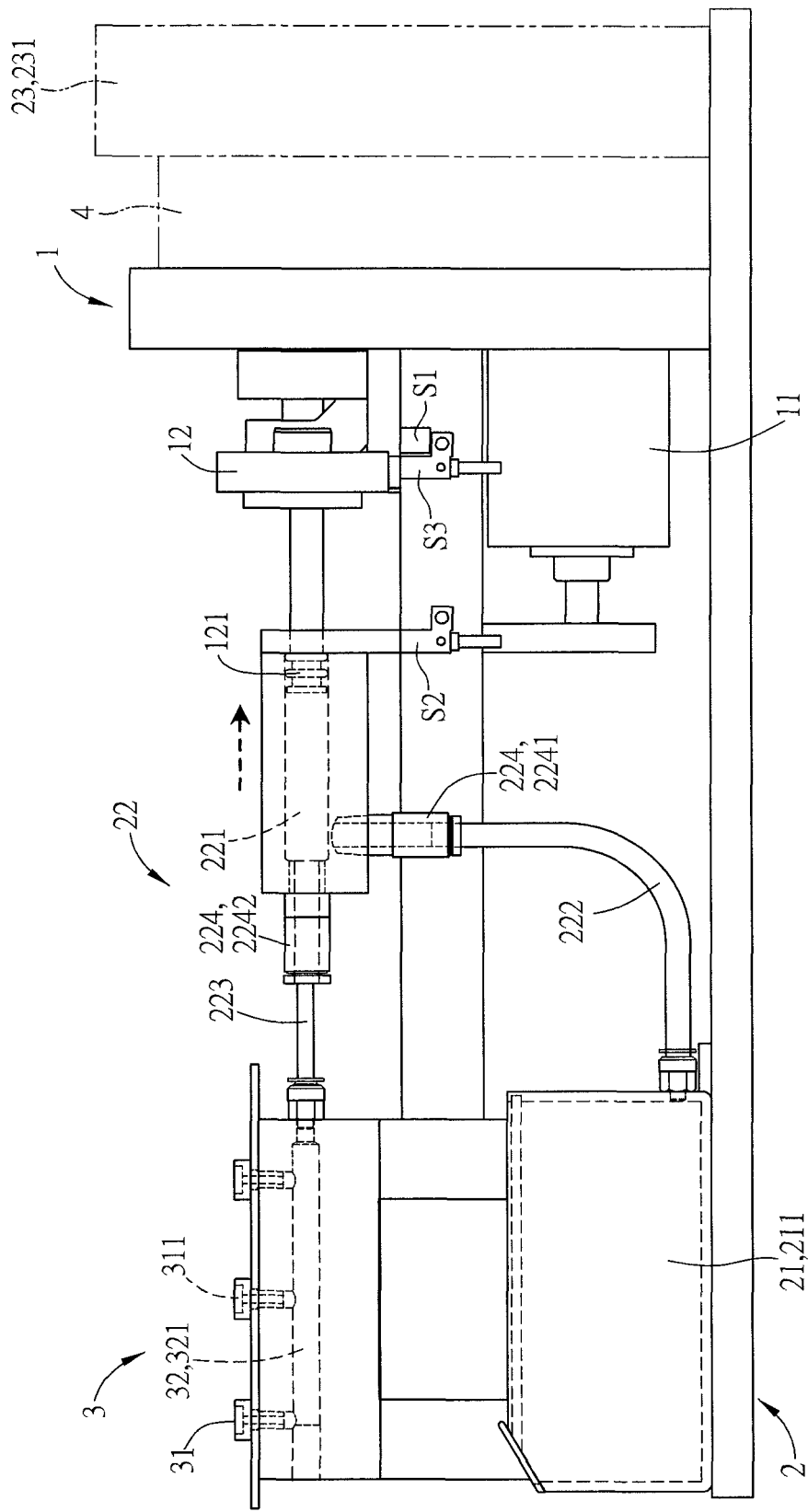
FIGS. 3A and 3B are schematic diagrams showing the operations of the manufacturing device of a test strip according to an embodiment of the disclosure.
Figure 3B:
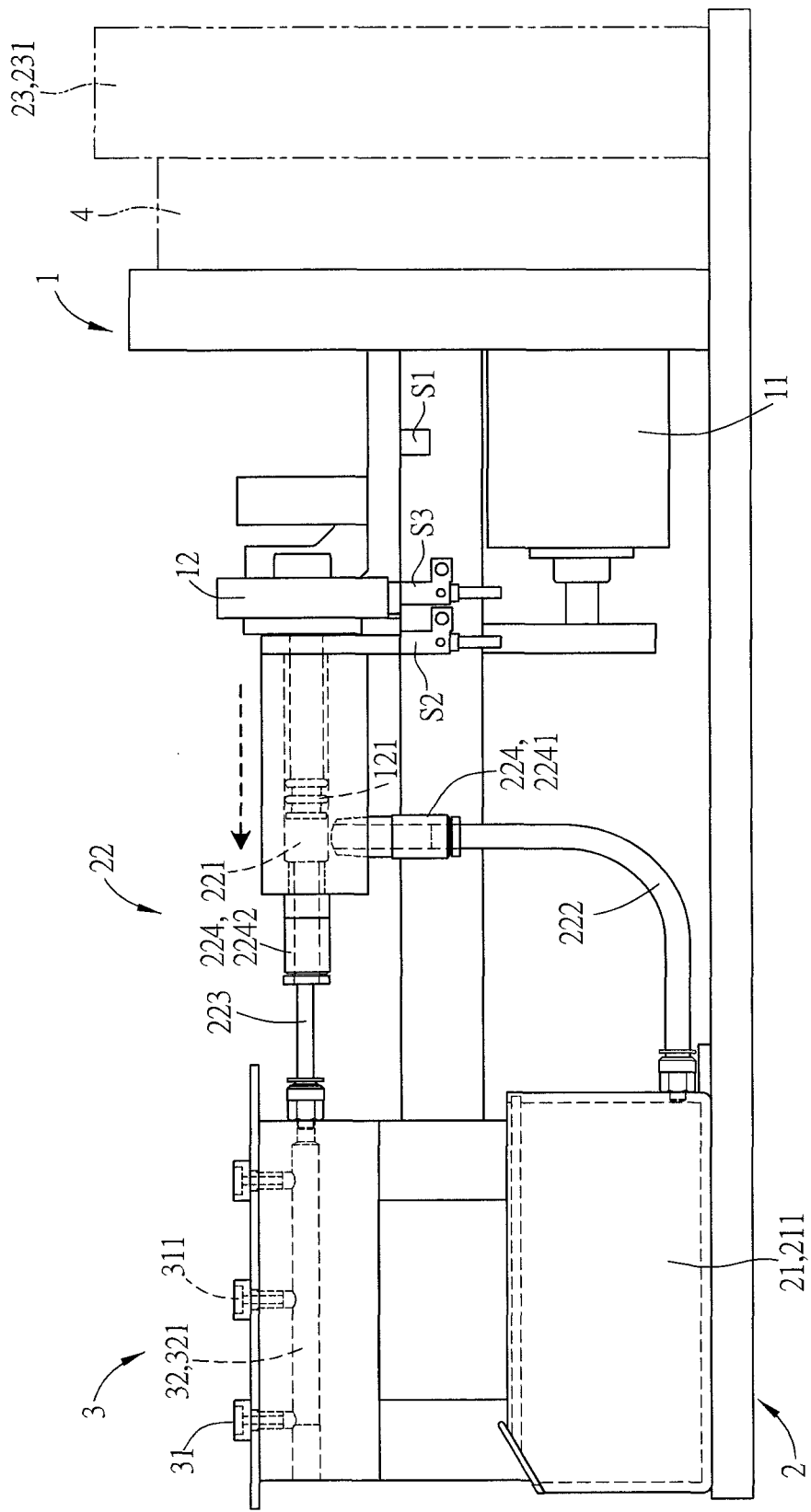

FIGS. 1A and 1B are schematic diagrams showing a manufacturing device of a test strip according to an embodiment of the disclosure. FIG. 2 is a schematic diagram showing the internal mechanisms of the manufacturing device of FIG. 1A. FIGS. 3A and 3B are schematic diagrams showing the operations of the manufacturing device of a test strip according to an embodiment of the disclosure.

As shown in FIGS. 1A, 1B, 2, 3A and 3B, a manufacturing device of a test strip D1 includes a fluid push module 1, a fluid flow module 2, and a fluid output module 3. The fluid push module 1 includes an actuator 11 and a transmission unit 12, and the actuator 11 is connected to the transmission unit 12. The transmission unit 12 has at least a fluid delivery member 121, which is disposed at one end of the transmission unit 12.

The fluid flow module 2 includes a reagent storage unit 21 and a reagent delivery unit 22. The reagent storage unit 21 has at least one reagent storage chamber 211. The reagent delivery unit 22 has at least one drain chamber 221, at least one first infusion line 222, at least one second infusion line 223, and a plurality of check valves 224. The fluid delivery member 121 is disposed in the drain chamber 221, and the first infusion line 222 is disposed between the reagent storage chamber 211 and the drain chamber 221 and communicates the reagent storage chamber 211 and the drain chamber 221. The check valves 224 are disposed at one ends of the first infusion line 222 and the second infusion line 223, respectively.

The fluid output module 3 includes a plurality of reagent outlets 31 and a reagent output unit 32. One end of each reagent outlet 31 is configured with an inner recess 311, and a reagent flow direction is opposite to a gravity direction. The reagent output unit 32 has a plurality of channels 321 corresponding to the reagent outlets 31. Each of the channels 321 is connected to another end of each reagent outlet 31 opposite to the inner recess 311. The second infusion line 223 is disposed between the drain chamber 221 and the reagent output unit 32 and communicates the drain chamber 221 and the reagent output unit 32.

Figure 6:
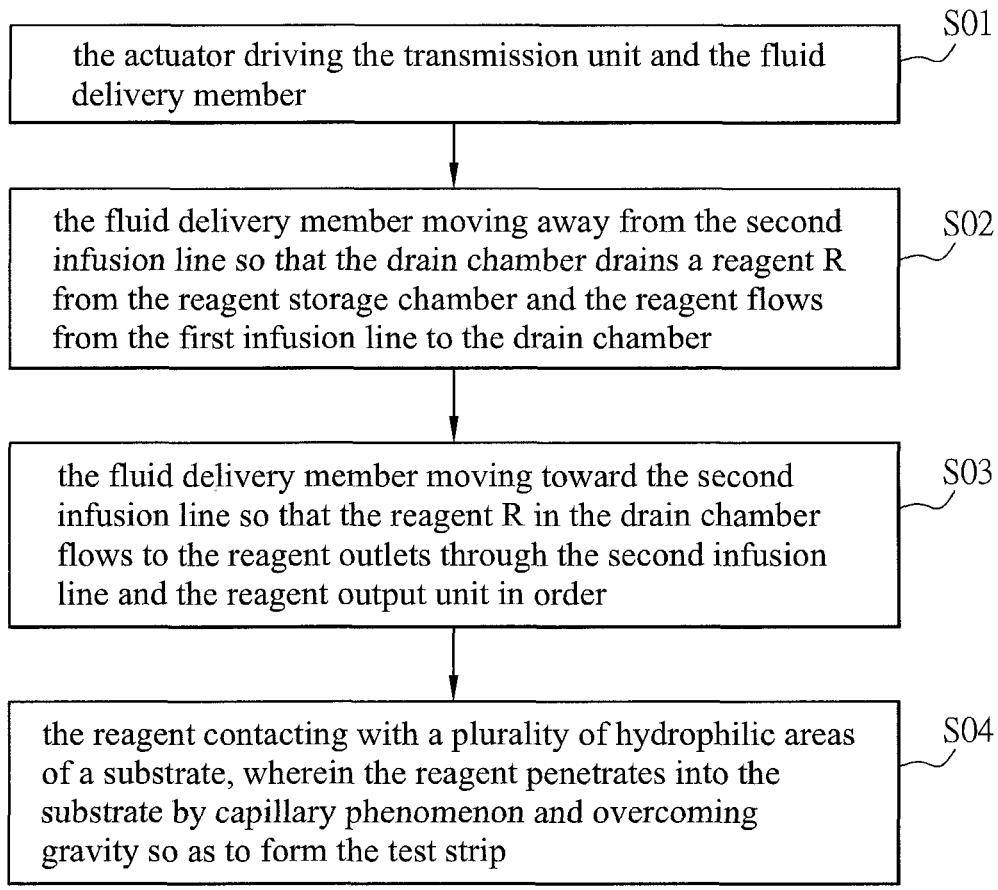
FIG. 6 is a flow chart of a manufacturing method of a test strip according to an embodiment of the disclosure.

As shown in FIG. 6, the present disclosure further provide a manufacturing method of a test strip, which is applied to the above-mentioned manufacturing device D1 for manufacturing a test strip. The manufacturing method includes the following steps of: the actuator 11 driving the transmission unit 12 and the fluid delivery member 121 (step S01); the fluid delivery member 121 moving away from the second infusion line 223 so that the drain chamber 221 drains a reagent R from the reagent storage chamber 211 and the reagent R flows from the first infusion line 222 to the drain chamber 221 (step S02); the fluid delivery member 121 moving toward the second infusion line 223 so that the reagent R in the drain chamber 221 flows to the reagent outlets 31 through the second infusion line 223 and the reagent output unit 32 in order (step S03); and the reagent R contacting with a plurality of hydrophilic areas P1 of a substrate P, wherein the reagent R penetrates into the substrate P by capillary phenomenon and overcoming gravity so as to form the test strip (step SO4). Herein, the substrate P is a blank strip before absorbing the reagent R, and the substrate P further has a plurality of hydrophobic areas P2 and a plurality of hydrophilic areas P1 corresponding to the reagent outlets 31.

Figure 4A:
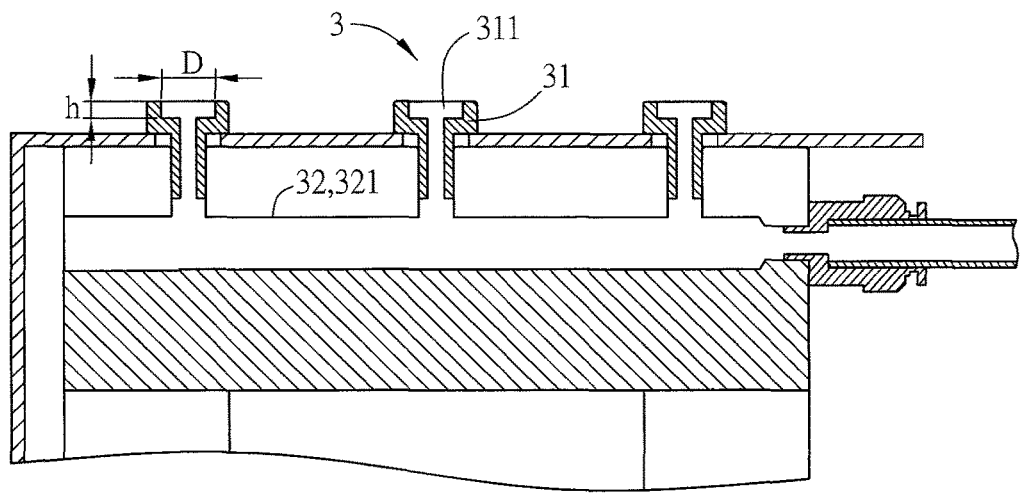
FIG. 4A is a sectional view of the fluid output module along the line A-A of FIG. 1A.
Figure 4B:
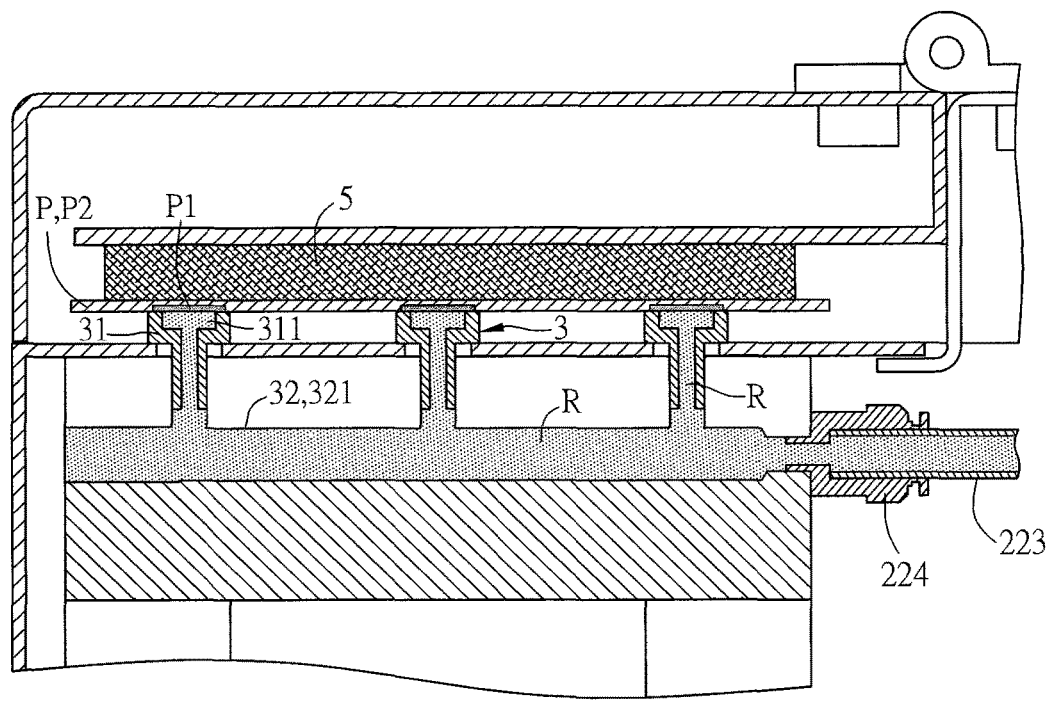
FIG. 4B is a schematic diagram showing the fluid output module of FIG. 4A cooperating with a strip.
Figure 7:
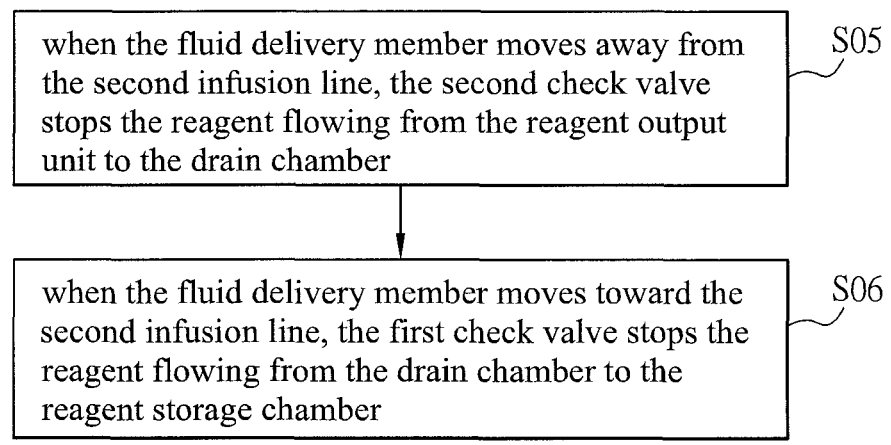
FIGS. 7 to 9 are flow chart of a manufacturing method of a test strip according to another embodiment of the disclosure.
Figure 8:
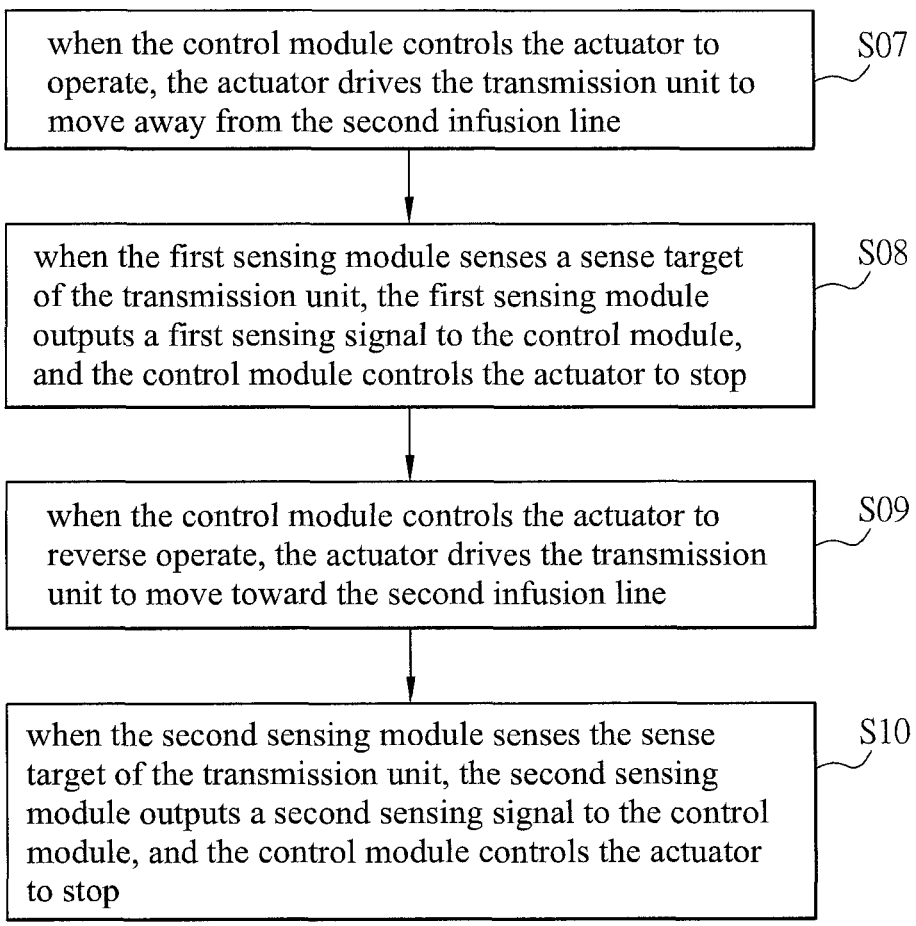
Figure 9:
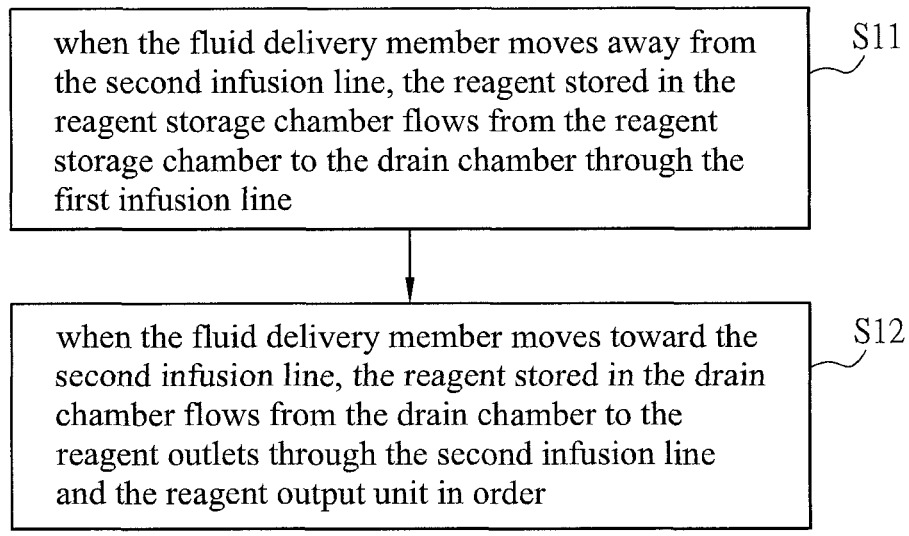

FIG. 4A is a sectional view of the fluid output module along the line A-A of FIG. 1A, and FIG. 4B is a schematic diagram showing the fluid output module of FIG. 4A cooperating with a strip. FIGS. 7 to 8 are flow chart of a manufacturing method of a test strip according to another embodiment of the disclosure. Referring to FIGS. 2, 3A, 3B, 4A, 4B, 7 and 8, the check valves 224 includes a first check valve 2241 and a second check valve 2242. The first check valve 2241 is disposed at one end of the first infusion line 222, and the second check valve 2242 is disposed at one end of the second infusion line 223. When the fluid delivery member 121 moves away from the second infusion line 223, the second check valve 2242 stops the reagent R flowing from the reagent output unit 32 to the drain chamber 221 (step S05). When the fluid delivery member 121 moves toward the second infusion line 223, the first check valve 2241 stops the reagent R flowing from the drain chamber 221 to the reagent storage chamber 211 (step S06). The one end of the first infusion line 222 is located close to the reagent storage chamber 211 or away from the drain chamber 221, and the one end of the second infusion line 223 is located close to the reagent storage chamber 211 or away from the drain chamber 221.

In this embodiment, the manufacturing device D1 further includes a control module 4 for controlling the actuator 11 to operate, to stop or to reverse operate. In this embodiment, the manufacturing device D1 further includes at least one first sensing module S1 disposed at one end of a back-and-forth path of the transmission unit 12. Besides, the manufacturing device D1 further includes at least one second sensing module S2 disposed at another end of the back-and-forth path of the transmission unit 12, which is opposite to the first sensing module.

When the control module 4 controls the actuator 11 to operate, the actuator 11 can drive the transmission unit 12 to move away from the second infusion line 223 (step S07). When the first sensing module S1 senses a sense target S3 of the transmission unit 12, the first sensing module S1 outputs a first sensing signal to the control module 4, and the control module 4 controls the actuator to stop (step S08). When the control module 4 controls the actuator 11 to reverse operate, the actuator 11 can drive the transmission unit 12 to move toward the second infusion line 223 (step S09). When the second sensing module S2 senses the sense target S3 of the transmission unit 12, the second sensing module S2 outputs a second sensing signal to the control module 4, and the control module 4 controls the actuator 11 to stop (step S10). The moving speeds of the actuator and the transmission unit can be controlled and adjusted by the control module so as to control the fluid delivery member to move toward the second infusion line in stepwise, thereby achieving the precisely control and micro amount output of the reagent. In addition, the configuration of the control module, the first sensing unit and the second sensing unit can control to stop the actuator or to change the operation direction of the actuator, and this can prevent the over moving (back and forth), which may cause the damage of the actuator.

As shown in FIGS. 1B, 4A and 4B, in this embodiment, the manufacturing device D1 further includes a pressure module 5 disposed corresponding to the reagent outlets 31. When the substrate P is placed outside the reagent outlets 31 and the upper cap of the manufacturing device D1 is closed, the pressure module 5 applies a pressure toward the reagent outlets 31. This pressure operation can absorb the tolerance between the reagent outlets 31 and tightly attach the substrate P to the regent outlets 31. In this case, the reagent R can contact with the plurality of hydrophilic areas P1 of the substrate P, and penetrate into the substrate P by capillary phenomenon and overcoming gravity so as to form the test strip.

In this embodiment, the reagent outlets 31 can be replaceable. For example, the reagent outlets 31 can be replaced by other reagent outlets having various sizes of inner recesses 311. The widths D of the inner recesses 311 of different sizes can control the contact surfaces between the reagent R in the inner recesses 311 and the substrate P, thereby adjusting the amount of the reagent R absorbed by the substrate P. In addition, if the delivering amount of the fluid delivery member toward the second infusion line 223 is fixed, the output amount of the reagent R in the inner recess 311 can be adjusted by the volume of the inner recess 311, which can be controlled by the different sizes of the height h and width D of the inner recess 311. In this embodiment, the direction of the inner recess 311 and the output direction of the reagent are opposite to the gravity direction, so that the output amount of the reagent R can be more precisely controlled. This design can prevent the excess output of the reagent R, which may overflow from the hydrophilic area P1 of the substrate P.

Referring to FIGS. 2, 3A, 3B, 4A, 4B and 9, the fluid flow module 2 and the fluid output module 3 together form at least a reagent transmission path, and the reagent transmission path is isolated. When the fluid delivery member 121 moves away from the second infusion line 223, the reagent R stored in the reagent storage chamber 211 flows from the reagent storage chamber 211 to the drain chamber 221 through the first infusion line 222 (step S11). When the fluid delivery member 121 moves toward the second infusion line 223, the reagent R stored in the drain chamber 221 flows from the drain chamber 221 to the reagent outlets 31 through the second infusion line 223 and the reagent output unit 32 in order (step S12). Besides, multiple of the reagent outlets 31 of the fluid output module 3 arranged in a row have a common one of the channels 321, the channel 321 corresponding to one row of the reagent outlets 31 is isolated from the reagent transmission path. When the fluid delivery member 121 moves toward the second infusion line 223, the reagent R flows to the corresponding row of reagent outlets 31 through the second infusion line 223 and the corresponding channel 321. Accordingly, the different rows of the reagent outlets can output different reagents for different testing targets by the cooperation of the reagent transmission paths and the reagent storage chambers. This configuration can provide the detection diversity of a single test strip.

Referring to FIGS. 2, 3A and 3B, in this embodiment, the fluid flow module 2 further includes a reagent supply unit 23 having at least one supply tank 231, and the supply tank 231 is communicated with the reagent storage chamber 211. When the fluid delivery member 121 moves away from the second infusion line 223, the reagent R stored in the supply tank 231 flows to the reagent storage chamber 211. In this embodiment, the supply tank 231 can be communicated with the reagent storage chamber 211 by a hollow tube (not shown).

As mentioned above, the appearance and size the manufacturing device of a test strip D1 of this disclosure can be similar to a microwave oven or a printer. This can sufficiently minimize the size of the manufacturing device and reduce the space for installing the manufacturing device D1.

Figure 5:
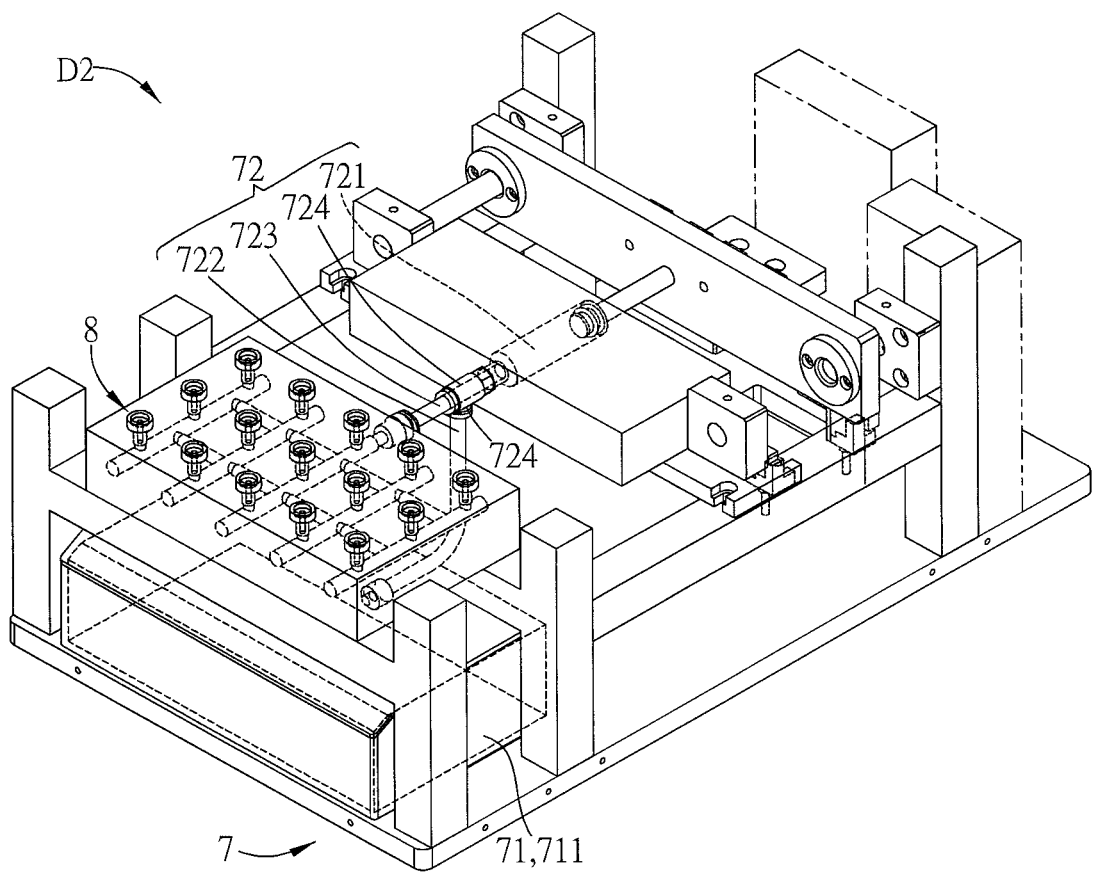
FIG. 5 is a schematic diagram showing a manufacturing device of a test strip according to another embodiment of the disclosure.

As shown in FIG. 5, a manufacturing device of a test strip D2 has a fluid flow module 7, which is simply a single reagent transmission path for cooperating with a fluid output module 8. A reagent storage unit 71 includes only one reagent storage chamber 711, and the reagent transmission unit 72 only includes a drain chamber 721, a first infusion line 722, a second infusion line 723, and two check valves 724, which form a single reagent transmission path. The simplified structure of the fluid flow module 7 can further reduce the size of the manufacturing device of a test strip D2.

In summary, the manufacturing device of a test strip of this disclosure has an inner recess design cooperated with the stepwise reagent delivering from the drain chamber, which is carried out by using the actuator to drive the fluid delivery member, so that different reagent output amounts can be provided. In addition, the manufacturing device of a test strip can adjust the stepwise delivery amount by controlling the actuator and the transmission unit in the back-and-forth path, thereby achieving the precisely control and micro amount output of the reagent. Moreover, the direction of the inner recess and the output direction of the reagent are opposite to the gravity direction, so that the output amount of the reagent can be more precisely controlled. This design can prevent the excess output of the reagent, which may overflow from the hydrophilic area of the substrate.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. A manufacturing device of a test strip, comprising:
a fluid push module comprising an actuator and a transmission unit, wherein the actuator is connected to the transmission unit, the transmission unit has at least a fluid delivery member, and the fluid delivery member is disposed at one end of the transmission unit;
a fluid flow module comprising a reagent storage unit and a reagent delivery unit, wherein the reagent storage unit has at least a reagent storage chamber, the reagent delivery unit has at least a drain chamber, at least a first infusion line, at least a second infusion line and a plurality of check valves, the fluid delivery member is disposed in the drain chamber, the first infusion line is disposed between the reagent storage chamber and the drain chamber and communicates the reagent storage chamber and the drain chamber, the check valves are disposed at one ends of the first infusion line and the second infusion line; and
a fluid output module comprising a plurality of reagent outlets and a reagent output unit, wherein one end of each of the reagent outlets is configured with an inner recess, a reagent flow direction is opposite to a gravity direction, the reagent output unit has a plurality of channels corresponding to the reagent outlets, each of the channels is connected to another end of each of the reagent outlets opposite to the inner recess, and the second infusion line is disposed between the drain chamber and the reagent output unit and communicates the drain chamber and the reagent output unit.

2. The manufacturing device of claim 1, wherein the check valves comprises:
a first check valve disposed at one end of the first infusion line; and
a second check valve disposed at one end of the second infusion line.

3. The manufacturing device of claim 1, wherein the fluid flow module and the fluid output module together form at least a reagent transmission path, and the reagent transmission path is isolated.

4. The manufacturing device of claim 1, wherein multiple of the reagent outlets arranged in a row have a common one of the channels.

5. The manufacturing device of claim 1, further comprising:
at least a first sensing module disposed at one end of a back-and-forth path of the transmission unit.

6. The manufacturing device of claim 5, further comprising:
at least a second sensing module disposed at another end of the back-and-forth path of the transmission unit, which is opposite to the first sensing module.

7. The manufacturing device of claim 1, further comprising:
a control module for controlling the actuator.

8. The manufacturing device of claim 1, further comprising:
a pressure module disposed corresponding to the reagent outlets.

9. The manufacturing device of claim 1, wherein the fluid flow module further comprises a reagent supply unit having at least a supply tank, and the supply tank is communicated with the reagent storage chamber.

10. A manufacturing method of a test strip applied to the manufacturing device of claim 1, the manufacturing method comprising steps of:
the actuator driving the transmission unit and the fluid delivery member;
the fluid delivery member moving away from the second infusion line so that the drain chamber drains a reagent from the reagent storage chamber and the reagent flows from the first infusion line to the drain chamber;
the fluid delivery member moving toward the second infusion line so that the reagent in the drain chamber flows to the reagent outlets through the second infusion line and the reagent output unit in order; and
the reagent contacting with a plurality of hydrophilic areas of a substrate, wherein the reagent penetrating into the substrate by capillary phenomenon and overcoming gravity so as to form the test strip.

11. The manufacturing method of claim 10, wherein the check valves comprises a first check valve and a second check valve, the first check valve is disposed at one end of the first infusion line, and the second check valve is disposed at one end of the second infusion line;
wherein, when the fluid delivery member moves away from the second infusion line, the second check valve stops the reagent flowing from the reagent output unit to the drain chamber, and when the fluid delivery member moves toward the second infusion line, the first check valve stops the reagent flowing from the drain chamber to the reagent storage chamber.

12. The manufacturing method of claim 10, wherein the fluid flow module and the fluid output module together form at least a reagent transmission path, and the reagent transmission path is isolated;
wherein, when the fluid delivery member moves away from the second infusion line, the reagent stored in the reagent storage chamber flow from the reagent storage chamber to the drain chamber through the first infusion line, and when the fluid delivery member moves toward the second infusion line, the reagent stored in the drain chamber flow from the drain chamber to the reagent outlets through the second infusion line and the reagent output unit in order.

13. The manufacturing method of claim 10, wherein the manufacturing device further comprises a control module for controlling the actuator to operate, to stop or to reverse operate.

14. The manufacturing method of claim 13, wherein the manufacturing device further comprises at least a first sensing module disposed at one end of a back-and-forth path of the transmission unit;
   wherein, when the first sensing module senses a sense target of the transmission unit, the first sensing module outputs a first sensing signal to the control module, and the control module controls the actuator to stop.

15. The manufacturing method of claim 14, wherein the manufacturing device further comprises at least a second sensing module disposed at another end of the back-and-forth path of the transmission unit, which is opposite to the first sensing module;
   wherein, when the second sensing module senses the sense target of the transmission unit, the second sensing module outputs a second sensing signal to the control module, and the control module controls the actuator to stop.

* * * * *